(12) United States Patent
Hung et al.

(10) Patent No.: US 11,302,419 B2
(45) Date of Patent: Apr. 12, 2022

(54) METHOD AND SYSTEM FOR DNA SEQUENCE ALIGNMENT

(71) Applicants: National Chiao Tung University, Hsinchu (TW); National Taiwan University, Taipei (TW)

(72) Inventors: Jui-Hung Hung, Tainan (TW); Chia-Hsiang Yang, New Taipei (TW); Yi-Chung Wu, Chiayi (TW)

(73) Assignees: National Chiao Tung University, Hsinchu (TW); National Taiwan University, Taipei (TW)

( * ) Notice: Subject to any disclaimer, the term of this patent is extended or adjusted under 35 U.S.C. 154(b) by 790 days.

(21) Appl. No.: 16/040,513

(22) Filed: Jul. 19, 2018

(65) Prior Publication Data

US 2019/0213301 A1 Jul. 11, 2019

(30) Foreign Application Priority Data

Jan. 5, 2018 (TW) ................................ 107100449

(51) Int. Cl.
*G16B 30/00* (2019.01)
*G16B 50/00* (2019.01)
*G16B 30/10* (2019.01)
*G16B 50/30* (2019.01)

(52) U.S. Cl.
CPC ............ *G16B 30/00* (2019.02); *G16B 30/10* (2019.02); *G16B 50/00* (2019.02); *G16B 50/30* (2019.02)

(58) Field of Classification Search
None
See application file for complete search history.

(56) References Cited

PUBLICATIONS

Chacon et al., n-step FM-Index for faster pattern matching, Procedia Computer Science 18 (2013) 70-79.*
Y. Sogabe, et al., "FPGA Acceleration of Short Read Mapping based on Sort and Parallel Comparison," Int. Conf. Field Programmable Logic and Applications (FPL), pp. 1-4, Sep. 2014.
J. Arram, et al., "Hardware Acceleration of Genetic Sequence Alignment," Int. Symp. Reconfigurable Computing: Architectures, Tools and Applications, pp. 13-24, Mar. 2013.
H. M. Waidyasooriya, et al., "Hardware-Acceleration of Short-Read Alignment Based on the Burrows-Wheeler Transform," IEEE Trans. Parallel and Distributed Systems, vol. 27, No. 5, pp. 1358-1372, May 2016.
Altschul et al., "Basic Local Alignment Search Tool", J. Mol. Biol. (May 1990) 215, pp. 403-410.
Homer et al., "BFAST: An Alignment Tool for Large Scale Genome Resequencing", PLoS ONE, Nov. 2009, vol. 4, Issue 11, total 12 pages.
Karkkainen, "Fast BWT in small space by blockwise suffix sorting", Theoretical Computer Science 387, Nov. 2007, pp. 249-257.
Burkhardt and Karkkainen, "Fast Lightweight Suffix Array Construction and Checking", CPM May 2003, LNCS 2676, pp. 55-69.
Ferragina and Manzini, "Opportunistic Data Structures with Applications", 2000 IEEE, Nov. 12-14, 2000, pp. 390-398.
Manber and Myers, "Suffix Arrays: A New Method for On-Line String Searches", Chapter 35, pp. 319-327, Oct. 1993.

* cited by examiner

*Primary Examiner* — Joseph Woitach
(74) *Attorney, Agent, or Firm* — MLO, a professional corp.

(57) ABSTRACT

A method for DNA sequence alignment is proposed to include steps of: generating multiple strings by acquiring foremost k number of suffixes corresponding to a reference DNA sequence; grouping the strings into multiple string groups; sorting the strings in each of the string groups to generate sorting results; obtaining sorted suffixes and a suffix array based on the sorting results; establishing FM-index data based on the sorted suffixes and the suffix array; and performing DNA sequence alignment on a target string based on the FM-index data to obtain an alignment result.

20 Claims, 10 Drawing Sheets

Reference DNA sequence

| C | A | T | G | C | A | A | $ |
|---|---|---|---|---|---|---|---|

Location indices — Suffixes

| Location indices | Suffixes | | | | | | |
|---|---|---|---|---|---|---|---|
| 0 | C | A | T | G | C | A | A | $ |
| 1 | A | T | G | C | A | A | $ | C |
| 2 | T | G | C | A | A | $ | C | A |
| 3 | G | C | A | A | $ | C | A | T |
| 4 | C | A | A | $ | C | A | T | G |
| 5 | A | A | $ | C | A | T | G | C |
| 6 | A | $ | C | A | T | G | C | A |
| 7 | $ | C | A | T | G | C | A | A |

FIG.2

| Location indices | Strings | | | |
|---|---|---|---|---|
| 0 | C | A | T | G |
| 1 | A | T | G | C |
| 2 | T | G | C | A |
| 3 | G | C | A | A |
| 4 | C | A | A | $ |
| 5 | A | A | $ | C |
| 6 | A | $ | C | A |
| 7 | $ | C | A | T |

FIG.3

| Location indices | Grouped strings | | | | |
|---|---|---|---|---|---|
| 5 | A | A | $ | C | |
| 6 | A | $ | C | A | First string group |
| 7 | $ | C | A | T | |

First splitter string →

| | | | | | |
|---|---|---|---|---|---|
| 0 | C | A | T | G | |
| 1 | A | T | G | C | Second string group |
| 4 | C | A | A | $ | |

Second splitter string →

| | | | | | |
|---|---|---|---|---|---|
| 2 | T | G | C | A | Third string group |
| 3 | G | C | A | A | |

FIG.4

Location
indices         Sorted strings

| 7 | $ | C | A | T |
| 6 | A | $ | C | A |
| 5 | A | A | $ | C |

First string group

| 1 | A | T | G | C |
| 4 | C | A | A | $ |
| 0 | C | A | T | G |

Second string group

| 3 | G | C | A | A |
| 2 | T | G | C | A |

Third string group

FIG.5

Location indices
(Suffix array)   Sorted suffixes

| 7 | $ | C | A | T | G | C | A | A |
| 6 | A | $ | C | A | T | G | C | A |
| 5 | A | A | $ | C | A | T | G | C |
| 1 | A | T | G | C | A | A | $ | C |
| 4 | C | A | A | $ | C | A | T | G |
| 0 | C | A | T | G | C | A | A | $ |
| 3 | G | C | A | A | $ | C | A | T |
| 2 | T | G | C | A | A | $ | C | A |

| CNT table | |
|---|---|
| Base-related character type (CNT-table address) | Recorded F-table address |
| A | 0 |
| C | 3 |
| G | 5 |
| T | 6 |

| Suffix array | |
|---|---|
| SA address | Location indices |
| 0 | 7 |
| 1 | 6 |
| 2 | 5 |
| 3 | 1 |
| 4 | 4 |
| 5 | 0 |
| 6 | 3 |
| 7 | 2 |

| F table | |
|---|---|
| F-table address | Character |
| 0 | $ |
| 1 | A |
| 2 | A |
| 3 | A |
| 4 | C |
| 5 | C |
| 6 | G |
| 7 | T |

| L table | |
|---|---|
| L-table address | Character |
| 0 | A |
| 1 | A |
| 2 | C |
| 3 | C |
| 4 | G |
| 5 | $ |
| 6 | T |
| 7 | A |

| OCC table | | | | |
|---|---|---|---|---|
| OCC-table address | Base-related character type | | | |
| | A | C | G | T |
| 0 | 1 | 0 | 0 | 0 |
| 1 | 2 | 0 | 0 | 0 |
| 2 | 2 | 1 | 0 | 0 |
| 3 | 2 | 2 | 0 | 0 |
| 4 | 2 | 2 | 1 | 0 |
| 5 | 2 | 2 | 1 | 0 |
| 6 | 2 | 2 | 1 | 1 |
| 7 | 3 | 2 | 1 | 1 |

L table

| L-table address | Character |
|---|---|
| 0 | A |
| 1 | A |
| 2 | C |
| 3 | C |
| 4 | G |
| 5 | $ |
| 6 | T |
| 7 | A |

Part of OCC table

| OCC-table address | Base-related character type | | | |
|---|---|---|---|---|
| | A | C | G | T |
| 0 | 1 | 0 | 0 | 0 |
| 4 | 2 | 2 | 1 | 0 |

CNT table

| Base-related character type (CNT-table address) | Recorded F-table address |
|---|---|
| A | 0 |
| C | 3 |
| G | 5 |
| T | 6 |

Part of suffix array

| SA address | Location indices |
|---|---|
| 0 | 7 |
| 4 | 4 |

METHOD AND SYSTEM FOR DNA SEQUENCE ALIGNMENT

CROSS-REFERENCE TO RELATED APPLICATION

This application claims priority of Taiwanese Invention Patent Application No. 107100449, filed on Jan. 5, 2018.

FIELD

The disclosure relates to a method and a system relating to data processing, and more particularly to a method and a system for DNA sequence alignment.

BACKGROUND

Deoxyribonucleic acid (DNA) sequencing is the process of determining the precise order of nitrogenous bases within a DNA molecule. DNA sequencing and DNA data analysis are now indispensable tools in the determination of the exact cause of genetic diseases and the development of associated treatments. Sequencing has become a routine analysis for genetics research and biomedical applications. The demand has driven the development of parallel sequencing, also known as next-generation sequencing (NGS). NGS is currently the fastest sequencing technique, taking about hours to sequence an entire human DNA. It can sequence the short fragments in a massively parallel fashion, achieving orders of magnitude higher throughput than the first-generation DNA sequencing technique based on Sanger sequencing. The applicable fields of NGS are vast and still expanding, and this technique fosters rapid advances in many fields related to the biomedical sciences. However, as the throughput of DNA sequencing grows exponentially, the succeeding data processing and analysis are ever more time consuming.

Several algorithms for NGS data analysis had been developed, such as BLAST (basic local alignment search tool, referenced to "Basic Local Alignment Search Tool," Journal of Molecular Biology, vol. 215, no. 3, pp. 403-410, May 1990) and BFAST (BLAT-like fast accurate search tool, referenced to "An Alignment Tool for Large Scale Genome Resequencing," PLoS ONE, vol. 4, no. 11, p. e7767, 2009). These early techniques still cost lots of processing time and are not suitable for short alignments. Some software packages for NGS data analysis utilize the Ferragina and Manzini (FM)-index, which contains the Burrows-Wheeler Transform (BWT) and its subsidiary data structure, to search for arbitrary short DNA sequences. Although FM-index achieves significant better alignment throughput, too much memory space is required.

SUMMARY

Therefore, an object of the disclosure is to provide a method that can alleviate at least one of the drawbacks of the prior art.

According to the disclosure, the method for DNA sequence alignment is proposed to be implemented by a processor and include steps of: (A) providing DNA sequencing data that relates to a reference DNA sequence which includes N number of characters, each being one of multiple base-related character types that relate to nucleotide bases of the reference DNA sequence, the DNA sequencing data including: N number of suffixes each of which has N number of characters respectively corresponding to the N number of characters of the reference DNA sequence, the suffixes being constructed by circularly shifting the characters of the reference DNA sequence; and N number of location indices each of which indicate a location of a respective one of the characters in the reference DNA sequence and corresponds to a respective one of the suffixes; obtaining N number of strings that respectively correspond to the suffixes, each of the strings being obtained by acquiring, from the corresponding one of the suffixes, foremost k number of the characters of the suffix, where N>k; sampling the strings to acquire P number of splitter strings; grouping the strings into (P+1) number of string groups based on lexicographical ordering of the strings relative to the splitter strings; sorting, for each of the string groups, strings in the string group in lexicographical order to obtain a sorting result; sorting the suffixes based on the sorting results for the string groups to obtain sorted suffixes, and obtaining a suffix array (SA) that includes N number of SA addresses respectively recording the location indices which respectively correspond to the sorted suffixes in order; establishing FM-index data in an FM-index data structure based on the suffix array and the sorted suffixes; and performing DNA sequence alignment on a target string based on the FM-index data to obtain one of a first alignment result and a second alignment result. The first alignment result indicates that the reference DNA sequence does not contain the target string, and the second alignment result includes at least one target index that is one of the location indices and that indicates a location in the reference DNA sequence where the target string is present.

Another object of the disclosure is to provide a system that can alleviate at least one of the drawbacks of the prior art.

According to the disclosure, the system is adapted for DNA sequence alignment with respect to DNA sequencing data that relates to a reference DNA sequence which includes N number of characters, each being one of multiple base-related character types that relate to nucleotide bases of the reference DNA sequence. The DNA sequencing data includes: N number of suffixes each of which has N number of characters respectively corresponding to the N number of characters of the reference DNA sequence, the suffixes being constructed by circularly shifting the characters of the reference DNA sequence; and N number of location indices each of which indicates a location of a respective one of the characters in the reference DNA sequence and corresponds to a respective one of the suffixes. The system includes a string generation module, a splitter string determining module, a grouping module, a string sorting module, a suffix array generation module, an FM-index data generation module and a searching module. The string generation module is disposed to receive the DNA sequencing data, and is configured to obtain N number of strings respectively corresponding to the suffixes, each of the strings being obtained by acquiring, from the corresponding one of the suffixes, foremost k number of the characters of the suffix, where N>k. The splitter string determining module is coupled to the string generation module for receiving the strings therefrom, and is configured to sample the strings to acquire P number of splitter strings. The grouping module is coupled to the string generation module for receiving the strings therefrom, and is configured to group the strings into (P+1) number of string groups based on lexicographical ordering of the strings relative to the splitter strings. The string sorting module is coupled to the grouping module for receiving the strings that are grouped into the (P+1) number of string groups therefrom, and is configured to sort, for each of the string groups, strings in the string group in lexicographical order to obtain a sorting result. The suffix array generation module is disposed to receive the suffixes, is coupled to the string sorting module for receiving the sorting results for the string groups therefrom, and is configured to sort the suffixes based on the sorting results for the string groups to obtain sorted suffixes, and obtain a suffix array (SA) that includes N number of SA addresses respectively recording the location indices which respectively correspond to the sorted suffixes in order. The FM-index data generation module is coupled to the suffix array generation module for receiving the sorted suffixes and the suffix array therefrom, and is configured to establish FM-index data in an FM-index data structure based on the suffix array and the sorted suffixes. The searching module is disposed to receive a target string, and is configured to perform DNA sequence alignment on the target string based on the FM-index data to obtain one of a first alignment result and a second alignment result. The first alignment result indicates that the reference DNA sequence does not contain the target string, and the second alignment result includes at least one target index that is one of the location indices and that indicates a location in the reference DNA sequence where the target string is present.

BRIEF DESCRIPTION OF THE DRAWINGS

Other features and advantages of the disclosure will become apparent in the following detailed description of the embodiment (s) with reference to the accompanying drawings, of which:

FIG. 2 is a schematic diagram exemplarily illustrating the reference DNA sequence and the corresponding suffixes and location indices;

FIG. 3 is a schematic diagram illustrating strings generated based on FIG. 2;

FIG. 4 is a schematic diagram illustrating grouping of the strings based on FIG. 3;

FIG. 5 is a schematic diagram illustrating sorting of the strings based on the grouping shown FIG. 3;

FIG. 8 is a schematic diagram illustrating sorted suffixes and a suffix array which are obtained by a suffix array generation module of the embodiment and which relate to the reference DNA sequence;

FIG. 9 is a schematic diagram illustrating FM-index data obtained based on FIG. 8; and FIG. 10 is a schematic diagram illustrating a part of the FM-index data which may be stored in a storage module in the embodiment.

DETAILED DESCRIPTION

Figure 1:
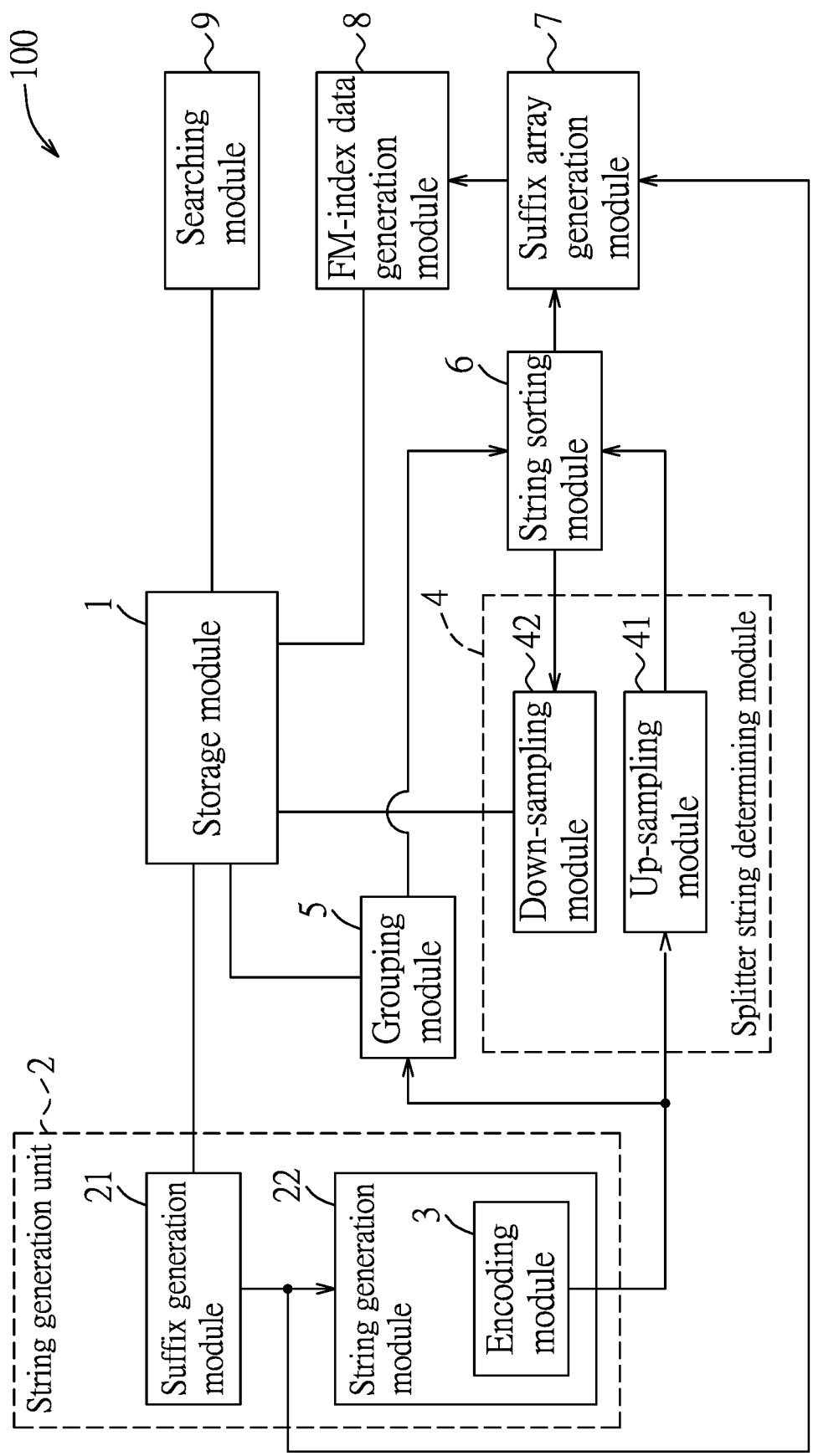
FIG. 1 is a block diagram illustrating an embodiment of a system adapted for DNA sequence alignment according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, the embodiment of a system 100 for DNA sequence alignment according to this disclosure is adapted for processing a reference DNA sequence, such as human DNA, but this disclosure is not limited in this respect.

The system 100 includes a storage module 1 (e.g., dynamic random access memory, static random access memory, flash memory, hard disk drive, or any type of device capable of data storage), a string generation unit 2 coupled to the storage module 1, a splitter string determining module 4 coupled to the storage module 1 and the string generation unit 2, a grouping module 5 coupled to the storage module 1 and the string generation unit 2, a string sorting module 6 coupled to the splitter string determining module 4 and the grouping module 5, a suffix array (SA) generation module 7 coupled to the string generation unit 2 and the string sorting module 6, an FM-index data generation module 8 coupled to the storage module 1 and the suffix array generation module 7, and a searching module 9 coupled to the storage module 1.

The storage module 1 stores the reference DNA sequence, which is represented by consecutive N number of characters, each of which is one of multiple base-related character types relating to nucleotide bases of the reference DNA sequence. In this embodiment, the base-related character types includes at least four character types of "A", "C", "G" and "T", which represent adenine, cytosine, guanine and thymine, respectively. In this embodiment, an additional character "$" is used after the N number of characters to indicate an end of the DNA sequence. Accordingly, this embodiment uses (N+1) number of characters, including the character "$", to perform data processing, such as sampling, grouping, sorting, etc., but this disclosure is not limited in this respect because use of the character "$" is not necessary. It is noted that, in practice, the reference DNA sequence may include characters other than "A", "C", "G" and "T" to represent nucleotide bases that are currently unconfirmed. The storage module 1 further stores (N+1) number of location indices, each of which indicates a location of a respective one of the (N+1) number of characters in relation to the reference DNA sequence. In this embodiment, the location indices are exemplified by 0 to N that respectively correspond to the (N+1) number of the characters in order, but this disclosure is not limited in this respect. Since a human DNA sequence contains about $3 \times 10^9$ nucleotide bases, a reference DNA sequence represented by seven characters (i.e., N=7) is exemplarily used to describe the embodiment hereinafter for the sake of brevity. Table 1 shows a relationship between the characters and the location indices.

TABLE 1

| | Location index | | | | | | | |
|---|---|---|---|---|---|---|---|---|
| | 0 | 1 | 2 | 3 | 4 | 5 | 6 | 7 |
| Nucleotide base (character) | C | A | T | G | C | A | A | $ |

The string generation unit 2 includes a suffix generation module 21 coupled to the storage module 1, and a string generation module 22 coupled to the suffix generation module 21. The suffix generation module 21 is configured to generate (N+1) number of suffixes based on the characters of the reference DNA sequence, and assigns the location indices to the suffixes respectively in order, so as to form DNA sequencing data. In this embodiment, each of the suffixes includes (N+1) number of characters, which include one character "$" and N number of characters respectively corresponding to the N number of characters of the reference DNA sequence, and the suffix generation module 21 generates the suffixes by circularly shifting the characters in relation to the reference DNA sequence (i.e., the (N+1) number of characters) from a leftmost character (a 5' end or 5' terminus) of the reference DNA sequence in order. Note that the suffix generation module 21 may generate only N number of suffixes each having N number of characters when the character "$" is not used, and the following operation may be adjusted accordingly in a similar way. Such adjustment should be simple to persons with ordinary skill in the art, so details thereof will be omitted hereinafter for the sake of brevity. FIG. 2 shows the suffixes generated by the suffix generation module 21 and the corresponding location indices based on Table 1. The string generation module 22 is coupled to the suffix generation module 21 for receiving the DNA sequencing data therefrom, and is configured to acquire, for each of the suffixes, foremost k number of the characters of the suffix, so as to obtain a respective string corresponding to the suffix, where N>k. In other words, the string generation module 22 generates (N+1) number of strings respectively corresponding to the (N+1) number of suffixes in total. In this embodiment, k=4, and FIG. 3 shows the strings acquired by the string generation module 22 and the corresponding location indices. It is noted that, in practice, the value of k may be determined based on a specification of the storage module 1, such as k=16, while N is about $3 \times 10^9$, which is much greater than k, so requirement for capacity of the storage module 1 (i.e., size of memory) may be significantly reduced in the subsequent process.

The splitter string determining module 4 is coupled to the string generation unit 2 for receiving the strings therefrom, and is configured to sample the strings to acquire P number of splitter strings. In this embodiment, the splitter string determining module 4 includes an up-sampling module 41 and a down-sampling module 42 that cooperate with the string sorting module 6 to acquire the P number of splitter strings. The up-sampling module 41 is coupled to the string generation module 22 for receiving the strings therefrom, is configured to acquire P×Q number of strings from the (N+1) number of strings arbitrarily, and is coupled to the string sorting module 5 for outputting the P×Q number of strings thereto. In one implementation, the up-sampling module 41 acquires the P×Q number of strings by acquiring P number of strings from the (N+1) number of strings arbitrarily for Q number of times. The string sorting module 6 sorts the P×Q number of strings in lexicographical order, and then outputs the sorted P×Q number of strings to the down-sampling module 42. The down-sampling module 42 is coupled to the string sorting module 6 for receiving the sorted P×Q number of strings therefrom, and is configured to choose one string from every Q number of the sorted P×Q number of strings in order, so as to obtain the P number of splitter strings that are arranged in order (e.g., ascending lexicographical order). The down-sampling module 42 is further coupled to the storage module 1 for storing the P number of splitter strings therein. In one implementation, the string generation module 22 may include an encoder module 3 configured to convert the different types of the characters into different digital codes in ascending order, so as to output the strings in a form of digital codes. For example, the characters "$", "A", "C", "G" and "T" may respectively be encoded as "000", "001", "010", "011" and "100", and the string sorting module 6 can sort the strings in ascending lexicographical order based on the values of the digital codes that represent the strings, but this disclosure is not limited in this respect. It is noted that the lexicographical order of the characters may be defined by users as desired, and is not necessarily the order of from "$", "A", "C", "G" to "T", which is exemplarily used in this embodiment. Based on FIG. 3, it is exemplified that the strings corresponding to the location indices "1" and "3" (e.g., the strings "ATGC" and "GCAA") are determined/chosen by the splitter string determining module 4 to be the splitter strings (i.e., P=2).

The grouping module 5 is coupled to the string generation module 2 for receiving the (N+1) number of strings therefrom, is coupled to the storage module 1, and is further configured to group the (N+1) number of strings into (P+1) number of string groups based on lexicographical ordering of the (N+1) number of strings relative to the splitter strings that are stored in the storage module 1. In detail, the grouping module 5 is configured to, for each of the strings: assign the string into a first one of the string groups when the string is smaller in lexicographical order than a first one of the splitter strings (one of the splitter strings that is smallest in lexicographical order); assign the string into a $(P+1)^{th}$ one of the string groups when the string is not smaller in lexicographical order than a $P^{th}$ one of the splitter strings (one of the splitter strings that is greatest in lexicographical order); and assign the string into a $j^{th}$ one of the string groups when the string is not smaller in lexicographical order than a $(j-1)^{th}$ one of the splitter strings and is smaller in lexicographical order than a $j^{th}$ one of the splitter strings, where j=2, 3, . . . , P. FIG. 4 shows a grouping result based on the strings shown in FIG. 3 and the exemplary splitter strings "ATGC" and "GCAA", which correspond to the location indices of "1" and "3", respectively. In this embodiment, the assignment for each of the strings is performed using binary search, but this disclosure is not limited in this respect.

The string sorting module 6 is further coupled to the grouping module 5 for receiving therefrom the strings that are grouped into the (P+1) number of string groups, and is configured to sort, for each of the string groups, the strings in the string group in lexicographical order (e.g., ascending lexicographical order) to obtain a sorting result. FIG. 5 shows the sorting result based on the grouping result shown in FIG. 4. In this embodiment, since the string sorting module 6 performs sorting group by group, complexity of sorting may be significantly reduced relative to sorting the entire (N+1) number of strings at one time.

Figure 6:
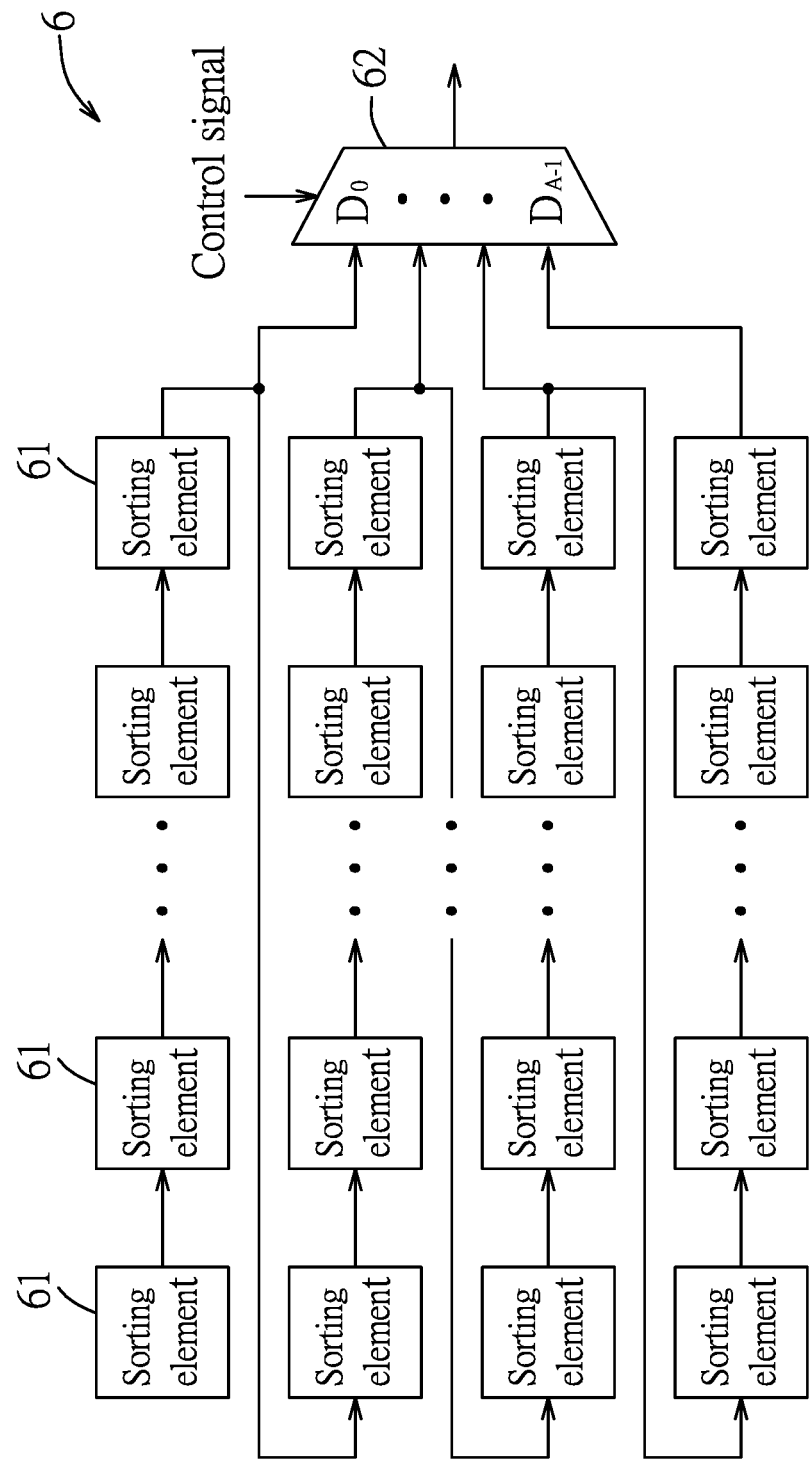
FIG. 6 is a block diagram illustrating a string sorting module of the embodiment.
Figure 7:
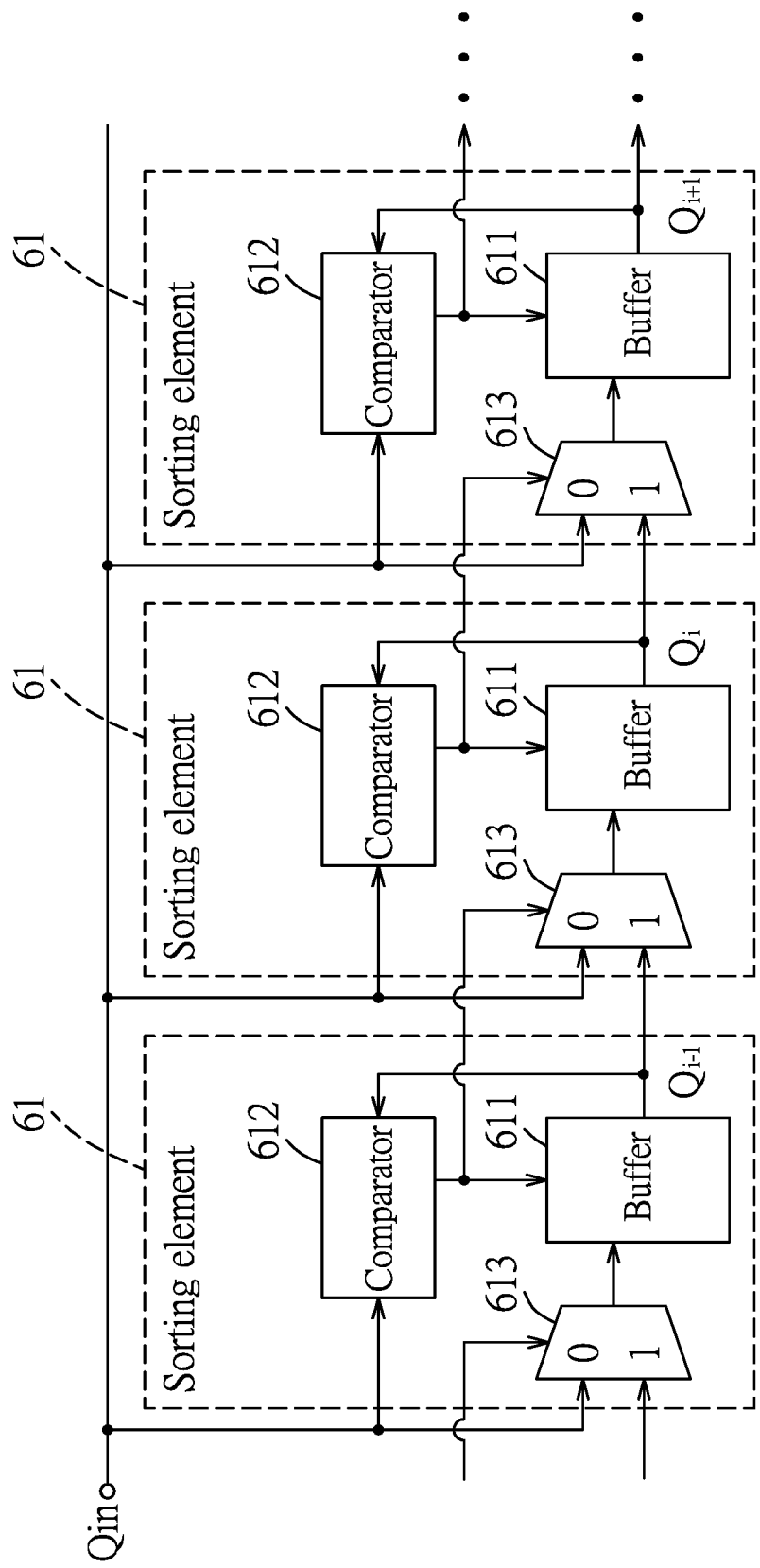
FIG. 7 is a block diagram illustrating connection of three sorting elements of the string sorting module of the embodiment.

Further referring to FIGS. 6 and 7, the string sorting module 6 includes C number of sorting elements 61 connected in a cascade manner, and an A-to-1 multiplexer 62. Each of the sorting elements includes a buffer 611, a comparator 612 and a 2-to-1 multiplexer 613. For each of the sorting elements 61, the buffer 611, which may be a D flip-flop, has an input terminal, a control terminal and an output terminal, and is configured to temporarily maintain a current data (e.g., $Q_{i-1}$, $Q_i$, $Q_{i+1}$ respectively for the sorting elements 61 in FIG. 7); the comparator 612 has a first input terminal disposed to receive to-be-sorted data (Qin), a second input terminal coupled to the output terminal of the buffer 611 of the (same) sorting element 61, and an output terminal coupled to the control terminal of the buffer 611 of the (same) sorting element 61; and the 2-to-1 multiplexer 613 has a first input terminal coupled to the first input terminal of the comparator 612 of the (same) sorting element 61, a second input terminal coupled to the output terminal of the buffer 611 of an immediate previous one of the sorting elements 61 (the left one of the sorting elements in FIG. 7), a control terminal coupled to the output terminal of the comparator 612 of the immediate previous one of the sorting elements 61, and an output terminal coupled to the input terminal of the buffer 611 of the (same) sorting element 61. In operation, for each of the sorting elements 61, which is exemplified as the central one of the sorting elements 61 in FIG. 7, the comparator 612 outputs, upon determining that the to-be-sorted data (Qin) is greater in the lexicographic order than the current data ($Q_i$) at the output terminal of the buffer 611, an enable signal to the control terminal of the buffer 611 of the sorting element 61 and the control terminal of the 2-to-1 multiplexer 613 of an immediate next one of the sorting elements 61 (the right sorting element 61 in FIG. 7) through the output terminal thereof, such that: the 2-to-1 multiplexer 613 of the immediate next one of the sorting elements 61 outputs the current data ($Q_i$) received from the buffer 611 of the sorting element 61 in response to the enable signal; and the buffer 611 of the sorting element 61 outputs, at the output terminal thereof in response to the enable signal, data received from the 2-to-1 multiplexer 613 of the sorting element 61 through the input terminal thereof. Furthermore, the comparator 612 outputs, upon determining that the to-be-sorted data (Qin) is smaller in lexicographic order than the current data ($Q_i$) at the output terminal of the buffer 611, a disable signal to the control terminal of the buffer 611 of the sorting element 61 and the control terminal of the 2-to-1 multiplexer 613 of the immediate next one of the sorting elements 61 through the output terminal thereof, such that: the 2-to-1 multiplexer 613 of the immediate next one of the sorting elements 61 outputs the to-be-sorted data (Qin) in response to the disable signal; and the buffer 611 of the sorting element 61 maintains the current data in response to the disable signal. For each of the sorting elements 61, data output by the 2-to-1 multiplexer 613 thereof is determined based on a signal from the comparator 612 of the immediate previous one of the sorting elements 61. To be clear, when that signal is the enable signal (e.g., a signal at a logic high level), the 2-to-1 multiplexer 613 outputs the current data ($Q_{i-1}$) at the output terminal of the buffer 611 of the immediate previous one of the sorting elements 61; and, when that signal is the disable signal (e.g., a signal at a logic low level), the 2-to-1 multiplexer 613 outputs the to-be-sorted data. According to such configuration of the sorting elements 61, the to-be-sorted data being smaller in lexicographical order (e.g., having a smaller value in digital codes) may be output earlier, achieving the purpose of sorting. It is noted that the string sorting module 6 may be used in two aspects:

1) sorting the P×Q number of strings received from the up-sampling module 41; and 2) sorting the strings for each of the string groups, which are received from the grouping module 5.

During the sorting operation, the string sorting module 6 may receive the to-be-sorted strings (either from the up-sampling module 41 or from the grouping module 5) one by one to serve as the to-be-sorted data. It is noted that, because the number of the sorting elements 61 is limited, uniformity of distribution of the (N+1) number of strings in the (P+1) number of string groups may affect complexity of the sorting operation for each sorting group. In this embodiment, the splitter strings determined by the up-and-down sampling scheme realized by the splitter string determining module 4 may cause a relatively uniform distribution of the number of strings for the string groups, so as to reduce complexity of sorting of the strings for each string group.

The A-to-1 multiplexer 62 has A number of input terminals $D_0$ to $D_{A-1}$, a control terminal disposed to receive a control signal relating to a total number D of the to-be-sorted data, and an output terminal. In this embodiment, an $m^{th}$ one of the input terminals of the A-to-1 multiplexer 62 is coupled to the output terminal of the buffer 611 of an $(m \times B)^{th}$ one of the sorting elements 61, where m=1, 2, . . . , A, but this disclosure is not limited in this respect. The A-to-1 multiplexer 62 is configured to, in response to the control signal: establish electrical connection between a first one of the input terminals thereof and the output terminal thereof when D≤B; establish electrical connection between an $(n+1)^{th}$ one of the input terminals thereof and the output terminal thereof when n×B<D≤(n+1)×B, where n=1, 2, . . . , A−1; and establish electrical connection between an $A^{th}$ one of the input terminals thereof and the output terminal thereof when C<D<2C. It is noted that, when C<D<2C, the string sorting module 6 performs sorting again (the second sorting) on (D−C) ones of the to-be-sorted data which are first outputted thereby (i.e., the overflow data) after completion of the sorting of all of the D number of to-be-sorted data (the first sorting). With the combination of the results of the first sorting and the second sorting, the D number of the to-be-sorted data (e.g., the P×Q number of strings from the up-sampling module 41 or the strings in one string group from the grouping module 5) may be accurately sorted. Use of the A-to-1 multiplexer 62 may reduce output latency for the to-be-sorted data of which the total number is smaller than C.

The suffix array generation module 7 is coupled to the suffix generation module 21 for receiving the suffixes therefrom, is coupled to the string sorting module 6 for receiving the sorting result for each of the string groups therefrom, and is configured to sort the suffixes based on the sorting result for each of the string groups to obtain sorted suffixes and obtain a suffix array (SA) that corresponds to the reference DNA sequence and that includes (N+1) number of SA addresses respectively recording the location indices which respectively correspond to the sorted suffixes in order. It is noted that, by merging the results of string sorting for the string groups (i.e., the sorting results), the sorting for the (N+1) number of the strings may be completed and in turn, and the sorting for the (N+1) number of the suffixes that respectively correspond to the (N+1) number of strings can also be done. FIG. 8 shows the suffix array and the sorted suffixes obtained by the suffix array generation module 7 based on the suffixes shown in FIG. 2 and the sorting result shown in FIG. 5.

The FM-index data generation module 8 is coupled to the suffix array generation module 7 for receiving the sorted suffixes and the suffix array therefrom, and is configured to establish FM-index data that corresponds to the reference DNA sequence in an FM-index data structure based on the suffix array and the sorted suffixes. In this embodiment, the FM-index data includes the suffix array, an F table, a CNT table, an L table and an OCC table, as shown in FIG. 9. The F table includes (N+1) number of F-table addresses which correspond in order to the sorted suffixes, and each of which records a first one of the characters of the corresponding one of the sorted suffixes. The CNT table includes a plurality of CNT-table addresses, each of which corresponds to a respective one of the base-related character types and records information relating to a start address in the F table for the respective one of the base-related character types. In this embodiment, each of the CNT-table addresses records an address immediately prior to the start address (i.e., start address minus one) in the F table for the respective one of the base-related character types. For example, in FIG. 9, the start addresses of the base-related character type "A", "C", "G" and "T" in the F table are "1", "4", "6" and "7", and the CNT-table addresses of the CNT table for the base-related character type "A", "C", "G" and "T" record "0", "3", "5" and "6", respectively. The L table includes (N+1) number of L-table addresses which correspond in order to the sorted suffixes, and each of which records a last one of the characters of the corresponding one of the sorted suffixes. The OCC table includes, for each of the base-related character types, (N+1) number of OCC-table addresses that respectively correspond to the L-table addresses in order. For each of the base-related character types, each of the OCC-table addresses records a number of occurrences of the base-related character type accumulated from the first one of the L-table addresses to one of the L-table addresses that corresponds to the OCC-table address. For example, the OCC-table address "3" for the base-related character type "A" records a number of occurrences of the base-related character type "A" accumulated from the L-table address "0" to the L-table address "3", which is "2" based on the L table shown in FIG. 9.

In practice, if the storage module 1 has sufficient storage capacity, the FM-index data generation module 8 may store the entire FM-index data in the storage module 1. Alternatively, the FM-index data generation module 8 may store only a part of the FM-index data in the storage module 1 in order to reduce the hardware requirement in terms of storage capacity. Since the CNT table is generated based on the F table, the OCC table is generated based on the L table and the suffix array is related to the OCC table, the part of the FM-index data stored in the storage module 1 may be constituted by at least the CNT table, the L table, a part of the suffix array and a part of the OCC table, which can be used to reconstruct the complete FM-index data. As an example, the FM-index data generation module 8 may down-sample the suffix array by retaining a first one of the SA addresses from every T1 number of the SA addresses to obtain the part of the suffix array, and down-sample the OCC table by retaining, for each of the base-related character types, a first one of the OCC-table addresses from every T2 number of the OCC-table addresses to obtain the part of the OCC table, where T1 and T2 are positive integers that may either be equal to or different from each other. FIG. 10 exemplarily shows the part of the FM-index data when T1=T2=4. By storing only the part of the FM-index data, storage capacity required for the FM-index data may be significantly reduced.

The searching module 9 is disposed to receive a target string that is to be aligned with the reference DNA sequence and that includes at least two characters belonging to the base-related character types, is coupled to the storage module 1 for acquiring the FM-index data, and is configured to perform DNA sequence alignment on the target string based on the FM-index data to obtain a first alignment result indicating that the reference DNA sequence does not contain the target string, or a second alignment result including at least one target index that is one of the location indices and that indicates a location in the reference DNA sequence where the target string is present (note that a target string may be present in one or more locations in the reference DNA sequence). In a case that the storage module 1 stores only the part of the FM-index data, the FM-index data may need to be reconstructed completely based on, for example, the CNT table, the L table, the part of the suffix array and the part of the OCC table prior to the searching operation in order to obtain the complete suffix array, the complete OCC table and the F table. In such case, the searching module 9 reads the part of the FM-index data stored in the storage module 1, and re-constructs the FM-index data using an FM-index data reconstruction algorithm. In this embodiment, the FM-index data reconstruction algorithm may be represented by:

$$OCC[n_{occ}, s] = OCC_D\left[\left\lfloor\frac{n_{occ}}{T2}\right\rfloor, s\right] + L\left[\left\lfloor\left\lfloor\frac{n_{occ}}{T2}\right\rfloor + 1, n_{occ}\right), s\right]; \text{ and}$$

$$SA[n_{SA}] = SA_D[CNT[L[n_{SA}]] + OCC[n_{SA}, L[n_{SA}]]] + 1,$$

where $n_{occ}$ represents an arbitrary one of the OCC-table addresses; S represents an arbitrary one of the base-related characters; OCC[.] represents a result of indexing operation on the OCC table; $OCC_D[.]$ represents a result of indexing operation on the part of the OCC table; L[.] represents a result of indexing operation on the L table; $n_{SA}$ represents an arbitrary one of the SA addresses; SA[.] represents a result of indexing operation on the suffix array; $SA_D[.]$ represents a result of indexing operation on the part of the suffix array; and CNT[.] represents a result of indexing operation on the CNT table. Accordingly, the searching module 9 may reconstruct the complete OCC table based on the L table, the part of the OCC table and T2, and reconstruct the complete suffix array based on the L table, the reconstructed OCC table and the part of the suffix array. Then, the searching module 9 may use a backward searching algorithm to search for the target string in the FM-index data completely stored in the storage module 1 or reconstructed thereby. In this embodiment, the target string is represented by "$S_1 S_2 \ldots S_M$", each of "$S_1$", "$S_2$", ..., "$S_M$" is a character, and the backward searching algorithm may be represented by:

$$S[i]=S_{(M-i)+1}, \text{ where } i=1,2,\ldots,M;$$

$$\text{index}_{min}[i]=CNT[S[i]]+OCC[\text{index}_{min}[i-1]-1,S[i]]+1;$$
and $$\text{index}_{max}[i]=CNT[S[i]]+OCC[\text{index}_{max}[i-1],S[i]]$$

where S[i] represents one of the characters of the target string to be searched for in an $i^{th}$ iterative searching operation; $\text{index}_{max}[i]$ represents a lower limit for the SA addresses obtained by the $i^{th}$ iterative searching operation; $\text{index}_{max}[i]$ represents an upper limit for the SA addresses obtained by the $i^{th}$ iterative searching operation; $\text{index}_{min}[0]$ is defined as zero; $\text{index}_{max}[0]$ is defined as N−1; and OCC[−1,S[1]] is defined as zero. By iteratively using the equations above for the characters of the target string one by one in a backward manner, the result of the DNA sequence alignment may be obtained.

In detail, the searching module 9 is configured to, after the $i^{th}$ iterative searching operation:

(I) perform, when i is smaller than M, an $(i+1)^{th}$ iterative searching operation upon determining that $\text{index}_{min}[i] \leq \text{index}_{max}[i]$;

(II) output the first alignment result upon determining that $\text{index}_{min}[i] > \text{index}_{max}[i]$;

(III) output the second alignment result upon determining that $\text{index}_{min}[M] = \text{index}_{max}[M]$, where the at least one target index includes one and only one target index which is one of the location indices that corresponds to either $\text{index}_{min}[M]$ or $\text{index}_{max}[M]$ for the suffix array; and (IV) output the second alignment result upon determining that $\text{index}_{min}[M] < \text{index}_{max}[M]$, where the at least one target index includes ($\text{index}_{max}[M] - \text{index}_{min}[M] + 1$) number of the target indices each of which is one of the location indices that corresponds to a respective one of the SA addresses which is not smaller than $\text{index}_{min}[M]$ and which is not greater than $\text{index}_{max}[M]$.

In operation, the searching module 9 first performs searching operation (the first iterative searching operation) on the last character "$S_M$" of the target string (i=1, S[1]=$S_M$), so as to acquire $\text{index}_{min}[1]$ and $\text{index}_{max}[1]$. It is noted that OCC[−1,$S_M$] is defined as zero since the OCC table only has the OCC-table addresses of 0 to N−1. Then, the searching module 9 determines whether index$_{min}$[1] is greater than index$_{max}$[1]. When determining that index$_{min}$[1] is greater than index$_{max}$[1], the searching module 9 determines that the target string is not present in the reference DNA sequence and outputs the first alignment result; and, when determining that index$_{min}$[1] is not greater than index$_{max}$[1], the searching module 9 causes i=i+1=2, and performs searching operation (the second iterative searching operation) on the character "$S_{M-1}$" of the target string (i=2, S[2]=$S_{M-1}$), so as to acquire index$_{min}$[2] and index$_{max}$[2]. Then, the searching module 9 determines whether index$_{min}$[2] is greater than index$_{max}$[2]. When determining that index$_{min}$[2] is greater than index$_{max}$[2], the searching module 9 determines that the target string is not present in the reference DNA sequence; and, when determining that index$_{min}$[2] is not greater than index$_{max}$[2], the searching module 9 causes i=i+1=3. The searching module 9 may perform the searching operation iteratively for each i=1, 2, . . . , M in the case that index$_{min}$[i] is not greater than index$_{max}$[i] in every iterative searching operation. In the $M^{th}$ iterative searching operation, the searching module 9 determines whether index$_{min}$[M] is greater than index$_{max}$[M]. When determining that index$_{max}$[M] is greater than index$_{max}$[M], the searching module 9 determines that the target string is not present in the reference DNA sequence and outputs the first alignment result. When determining that index$_{min}$[M] is equal to index$_{max}$[M], the searching module 9 may perform indexing operation on the suffix array according to index$_{min}$[M] or index$_{max}$[M], thereby obtaining one and the only one target index, which is one of the location indices that corresponds to the SA address of index$_{min}$[M] or index$_{max}$[M] for the suffix array (i.e., SA[index$_{min}$[M]] or SA[index$_{max}$[M]]), and outputting the second alignment result that includes the target index indicating a location in the reference DNA sequence where the target string is present. When determining that index$_{min}$[M] is smaller than index$_{max}$[M], the searching module 9 may perform indexing operation on the suffix array according to index$_{min}$[M], index$_{min}$[M]+1, . . . index$_{max}$[M], thereby obtaining (index$_{max}$[M]−index$_{min}$[M]+1) number of target indices, each of which is one of the location indices that corresponds to a respective one of the SA addresses ranging from index$_{min}$[M] to index$_{max}$[M] (index$_{min}$[M] and index$_{max}$[M] are included in the range) for the suffix array (i.e., SA[index$_{min}$[M]], SA[index$_{max}$[M]+1], . . . , SA[index$_{max}$[M]]), and outputting the second alignment result that includes the target indices each of which indicates a respective location in the reference DNA sequence where the target string is present.

For ease of understanding, as an example, the system 100 (see FIG. 1) of this disclosure is exemplarily used to perform DNA sequence alignment on a target string "CA" with reference to the FM-index data as shown in FIG. 9. In such a case, M=2, index$_{min}$[0]=0 and index$_{max}$[0]=7.

In the first iterative searching operation, S[1]=A, index$_{min}$[1]=CNT[A]+OCC[index$_{min}$[0]−1,A]+1=0+0+1=1, and index$_{max}$[1]=CNT[A]+OCC[index$_{max}$[0],A]=0+3=3. Since index$_{max}$[1] is greater than index$_{min}$[1], the searching module 9 proceeds to perform the second iterative searching operation.

In the second iterative searching operation, S[2]=C, index$_{min}$[2]=CNT[C]+OCC[index$_{min}$[1]−1,C]+1=3+OCC[0,C]+1=3+0+1=4, and index$_{max}$[2]=CNT[C]+OCC[index$_{max}$[1],C]=3+OCC[3,C]=3+2=5. Since index$_{max}$[1] is greater than index$_{min}$[1], the searching module 9 proceeds to perform the second iterative searching operation. Accordingly, the searching module 9 may output the second alignment result including two target indices of SA[index$_{min}$[2]] and SA[index$_{max}$[2]], which are SA[4]=4 and SA[5]=5, respectively. Referring to FIG. 2, it can be seen that the target string "CA" is present at the locations corresponding to the location indices "0" and "4" in the reference DNA sequence "CATGCAA$".

In summary, the system 100 for DNA sequence alignment according to this disclosure forms the strings by acquiring the foremost k number of the suffixes corresponding to the reference DNA sequence for the subsequent grouping and sorting operations, thereby significantly reducing storage capacity (e.g., memory size) required for storing the FM-index data, especially when N is significantly greater than k. Storage of a part of the FM-index data in cooperation of the FM-index data reconstruction algorithm may further reduce storage capacity required for storing the FM-index data. The up-and-down sampling scheme may aid in obtaining a relatively uniform distribution of the strings in the string groups, so as to reduce complexity of sorting. Accordingly, when the system and the method of this disclosure are applied to DNA sequence alignment, the task may be completed with relatively low hardware requirement and relatively short execution time.

The described operations of the string generation unit 2, the splitter string determining module 4, the grouping module 5, the string sorting module 6, the suffix array generation module 7, the FM-index data generation module 8 and the searching module 9 may be implemented as a method, apparatus, logic circuit or computer readable storage medium using standard programming and/or engineering techniques to produce software, firmware, hardware, or any combination thereof. The described operations may be implemented as code or logic maintained in a "computer readable storage medium", which may directly execute the functions or a processor may read and execute the code from the computer storage readable medium. The computer readable storage medium includes at least one of electronic circuitry, storage materials, inorganic materials, organic materials, biological materials, a casing, a housing, a coating, and hardware. A computer readable storage medium may be the storage module 1, and may include, but is not limited to, a magnetic storage medium (e.g., hard disk drives, floppy disks, tape, etc.), optical storage (CD-ROMs, DVDs, optical disks, etc.), volatile or non-volatile memory devices (e.g., EEPROMs, ROMs, PROMs, RAMs, DRAMs, SRAMs, flash memory, firmware, programmable logic, etc.), solid state devices (SSD), etc. The computer readable storage medium may further comprise digital logic implemented in a hardware device (e.g., an integrated circuit chip, a programmable logic device, a programmable gate array (PGA), field-programmable gate array (FPGA), application specific integrated circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, radio waves, infrared signals, Bluetooth, etc. The program code embedded on a computer readable storage medium may be transmitted as transmission signals from a transmitting station or computer to a receiving station or computer. A computer readable storage medium is not comprised solely of transmission signals, but includes tangible components, such as hardware elements. Those skilled in the art will recognize that many modifications may be made to this configuration without departing from the scope of the present disclosure, and that the article of manufacture may comprise suitable information bearing medium known in the art.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for DNA sequence alignment, implemented by a processor and comprising steps of:
   (A) providing a DNA sequencing data that relates to a reference DNA sequence which includes first to $N^{th}$ characters, each being one of multiple base-related character types that relate to nucleotide bases of the reference DNA sequence, where N is a positive integer, and the DNA sequencing data includes:
      first to $N^{th}$ suffixes, each of which has first to $N^{th}$ characters respectively corresponding to the first to $N^{th}$ characters of the reference DNA sequence, the first to $N^{th}$ suffixes being constructed by circularly shifting the first to $N^{th}$ characters of the reference DNA sequence; and
      first to $N^{th}$ location indices, each of which indicate a location of a respective one of the first to $N^{th}$ characters in the reference DNA sequence and corresponds to a respective one of the first to $N^{th}$ suffixes;
   (B) obtaining first to $N^{th}$ strings that correspond respectively to the first to $N^{th}$ suffixes, each of the first to $N^{th}$ strings being obtained by acquiring the first to $k^{th}$ characters of the corresponding one of the first to $N^{th}$ suffixes, where N>k;
   (C) sampling the first to $N^{th}$ strings to acquire P number of splitter strings, where P is a user-defined positive integer smaller than N;
   (D) grouping the first to $N^{th}$ strings into (P+1) number of string groups based on lexicographical ordering of the first to $N^{th}$ strings relative to the splitter strings;
   (E) sorting, for each of the string groups, strings in the string group in lexicographical order to obtain a sorting result;
   (F) sorting the first to $N^{th}$ suffixes based on the sorting results for the string groups to obtain sorted first to $N^{th}$ suffixes, and obtaining a suffix array (SA) that includes first to $N^{th}$ SA addresses respectively recording the first to $N^{th}$ location indices which respectively correspond to the sorted first to $N^{th}$ suffixes in order;
   (G) establishing FM-index data in an FM-index data structure based on the suffix array and the sorted first to $N^{th}$ suffixes; and
   (H) performing DNA sequence alignment on a target string based on the FM-index data to obtain one of a first alignment result and a second alignment result, wherein the first alignment result indicates that the reference DNA sequence does not contain the target string, and the second alignment result includes at least one target index that is one of the first to $N^{th}$ location indices and that indicates a location in the reference DNA sequence where the target string is present.

2. The method of claim 1, wherein step (A) includes:
   generating the first to $N^{th}$ suffixes by circularly shifting the first to $N^{th}$ characters of the reference DNA sequence from a 5' end of the reference DNA sequence in order; and
   assigning the first to $N^{th}$ location indices to the first to $N^{th}$ suffixes in order.

3. The method of claim 1, wherein step (C) includes:
   acquiring P×Q number of strings from the first to $N^{th}$ strings arbitrarily where Q is a user-defined positive integer;
   sorting the P×Q number of strings in lexicographical order; and
   choosing one string from every Q number of the P×Q number of strings thus sorted to obtain the P number of splitter strings.

4. The method of claim 3, wherein the acquiring the P×Q number of strings includes: acquiring P number of strings from the first to $N^{th}$ strings arbitrarily for Q number of times.

5. The method of claim 1, wherein the P number of splitter strings are arranged in ascending lexicographical order, and step (D) includes, for each of the first to $N^{th}$ strings:
   assigning said each of the first to $N^{th}$ strings into a first one of the string groups when said each of the first to $N^{th}$ strings is smaller in lexicographical order than a first one of the splitter strings;
   assigning said each of the first to $N^{th}$ strings into a $(P+1)^{th}$ one of the string groups when said each of the first to $N^{th}$ strings is not smaller in lexicographical order than a $P^{th}$ one of the splitter strings; and
   assigning said each of the first to $N^{th}$ strings into a $j^{th}$ one of the string groups when said each of the first to $N^{th}$ strings is not smaller in lexicographical order than a $(j-1)^{th}$ one of the splitter strings and is smaller in lexicographical order than a $j^{th}$ one of the splitter strings, where j=2, 3, . . . , P.

6. The method of claim 1, wherein the target string is represented by characters of $S_1$ to $S_M$ that are arranged in the given order, where 1≤M≤N;
   wherein the FM-index data includes:
      the suffix array;
      an F table including first to $N^{th}$ F table addresses which correspond in order to the sorted first to $N^{th}$ suffixes and each of which records a first one of the characters of the corresponding one of the sorted first to $N^{th}$ suffixes;
      a CNT table including a plurality of CNT-table addresses, each of which corresponds to a respective one of the base-related character types and records information relating to a start address in the F table for the respective one of the base-related character type;

an L table including first to $N^{th}$ L table addresses which respectively correspond to the sorted first to $N^{th}$ suffixes in order and each of which records a last one of the characters of the corresponding one of the sorted first to $N^{th}$ suffixes; and an OCC table including, for each of the base-related character types, first to $N^{th}$ OCC-table addresses that respectively correspond to the first to $N^{th}$ L-table addresses in order; and, for each of the base-related character types, each of the first to $N^{th}$ OCC-table addresses records a number of occurrences of the base-related character type accumulated from the first one of the L-table addresses address to one of the first to $N^{th}$ L-table addresses that corresponds to the OCC-table address;

wherein the DNA sequence alignment in step (H) is performed according to:

$$S[i]=S_{(M-i)+1}, \text{ where } i=1,2,\ldots,M;$$

$$\text{index}_{min}[i]=CNT[S[i]]+OCC[\text{index}_{min}[i-1]-1,S[i]]+1;$$
and $$\text{index}_{max}[i]=CNT[S[i]]+OCC[\text{index}_{max}[i-1],S[i]]$$

where S[i] represents one of the characters of the target string to be searched for in an $i^{th}$ iterative searching operation; $\text{index}_{min}$ [i] represents a lower limit for the first to $N^{th}$ SA addresses obtained by the $i^{th}$ iterative searching operation; $\text{index}_{max}$ [i] represents an upper limit for the first to $N^{th}$ SA addresses obtained by the $i^{th}$ iterative searching operation; CNT[.] represents a result of indexing operation on the CNT table; OCC[.] represents a result of indexing operation on the OCC table; $\text{index}_{min}$ [0] is defined as zero; $\text{index}_{max}$ [0] is defined as N−1; and OCC[−1,S[1]] is defined as zero; and wherein step (H) includes, after the $i^{th}$ iterative searching operation:

performing, when i is not greater than M, an $(i+1)^{th}$ iterative searching operation upon determining that $\text{index}_{min}$ [i]≤$\text{index}_{max}$ [i];

outputting the first alignment result upon determining that $\text{index}_{min}$ [i]>$\text{index}_{max}$ [i];

outputting the second alignment result upon determining that $\text{index}_{min}$ [M]=$\text{index}_{max}$ [M], wherein the at least one target index includes one and only one target index which is one of the first to $N^{th}$ location indices that corresponds to either $\text{index}_{min}$ [M] or $\text{index}_{max}$ [M] for the suffix array; and outputting the second alignment result upon determining that $\text{index}_{min}$ [M]<$\text{index}_{max}$ [M], wherein the at least one target index includes a plurality of the target indices each of which is one of the first to $N^{th}$ location indices that corresponds to a respective one of the first to $N^{th}$ SA addresses which is not smaller than $\text{index}_{min}$ [M] and which is not greater than $\text{index}_{max}$ [M].

7. A system adapted for DNA sequence alignment with respect to DNA sequencing data that relates to a reference DNA sequence which includes first to $N^{th}$ characters, each being one of multiple base-related character types that relate to nucleotide bases of the reference DNA sequence, where N is a positive integer, and the DNA sequencing data includes:

first to $N^{th}$ suffixes each of which has first to $N^{th}$ characters respectively corresponding to the first to $N^{th}$ characters of the reference DNA sequence, the first to $N^{th}$ suffixes being constructed by circularly shifting the first to $N^{th}$ characters of the reference DNA sequence; and first to $N^{th}$ location indices each of which indicates a location of a respective one of the first to $N^{th}$ characters in the reference DNA sequence and corresponds to a respective one of the first to $N^{th}$ suffixes;

said system comprising:

a string generation module disposed to receive the DNA sequencing data, and configured to obtain first to $N^{th}$ strings that correspond respectively to the first to $N^{th}$ suffixes, each of the first to $N^{th}$ strings being obtained by acquiring the first to $k^{th}$ characters of the corresponding one of the first to $N^{th}$ suffixes, where N>k;

a splitter string determining module coupled to said string generation module for receiving the first to $N^{th}$ strings therefrom, and configured to sample the first to $N^{th}$ strings to acquire P number of splitter strings, where P is a user-defined positive integer smaller than N;

a grouping module coupled to said string generation module for receiving the first to $N^{th}$ strings therefrom, and configured to group the first to $N^{th}$ strings into (P+1) number of string groups based on lexicographical ordering of the first to $N^{th}$ strings relative to the splitter strings;

a string sorting module coupled to said grouping module for receiving the first to $N^{th}$ strings that are grouped into the (P+1) number of string groups therefrom, and configured to sort, for each of the string groups, strings in the string group in lexicographical order to obtain a sorting result;

a suffix array generation module disposed to receive the first to $N^{th}$ suffixes, coupled to said string sorting module for receiving the sorting results for the string groups therefrom, and configured to sort the first to $N^{th}$ suffixes based on the sorting results for the string groups to obtain sorted first to $N^{th}$ suffixes and obtain a suffix array (SA) that includes first to $N^{th}$ SA addresses respectively recording the first to $N^{th}$ location indices which respectively correspond to the sorted first to $N^{th}$ suffixes in order;

an FM-index data generation module coupled to said suffix array generation module for receiving the sorted first to $N^{th}$ suffixes and the suffix array therefrom, and configured to establish FM-index data in an FM-index data structure based on the suffix array and the sorted first to $N^{th}$ suffixes; and a searching module disposed to receive a target string, and configured to perform DNA sequence alignment on the target string based on the FM-index data to obtain one of a first alignment result and a second alignment result, wherein the first alignment result indicates that the reference DNA sequence does not contain the target string, and the second alignment result includes at least one target index that is one of the first to $N^{th}$ location indices and that indicates a location in the reference DNA sequence where the target string is present.

8. The system of claim 7, further comprising a storage module electrically coupled to said splitter string determining module and said grouping module, and configured to store the reference DNA sequence and the first to $N^{th}$ location indices;

wherein said storage module receives and store the P number of splitter strings from said splitter string determining module; and wherein said grouping module groups on the first to $N^{th}$ strings based on the splitter strings stored in said storage module.

9. The system of claim 8, further comprising:
a suffix generation module coupled to said storage module, and configured to generate the first to $N^{th}$ suffixes by circularly shifting the first to $N^{th}$ characters of the reference DNA sequence from a 5' end of the reference DNA sequence in order, and to assign the first to $N^{th}$ location indices to the first to $N^{th}$ suffixes in order, so as to form the DNA sequencing data;
wherein said suffix generation module is further coupled to said string generation module for providing the DNA sequencing data thereto.

10. The system of claim 8, wherein said splitter string generation module is further coupled to said string sorting module, and includes
an up-sampling module coupled to said string generation module for receiving the first to $N^{th}$ strings therefrom, configured to acquire P×Q number of strings from the first to $N^{th}$ strings arbitrarily, and coupled to said string sorting module for outputting the P×Q number of strings thereto, where Q is a user-defined positive integer;
wherein said string sorting module is further configured to sort the P×Q number of strings in lexicographical order; and
wherein said splitter string generation module further includes a down-sampling module coupled to said string sorting module for receiving the P×Q number of strings thus sorted therefrom, configured to choose one string from every Q number of the P×Q number of strings thus sorted to obtain the P number of splitter strings, and coupled to said storage module for storing the P number of splitter strings therein.

11. The system of claim 10, wherein said up-sampling module is configured to acquire the P×Q number of strings by acquiring P number of strings from the first to $N^{th}$ strings arbitrarily for Q number of times.

12. The system of claim 8, wherein the P number of splitter strings are arranged in ascending lexicographical order, and said grouping module is configured to, for each of the first to $N^{th}$ strings:
assign said each of the first to $N^{th}$ strings into a first one of the string groups when said each of the first to $N^{th}$ strings is smaller in lexicographical order than a first one of the splitter strings;
assign said each of the first to $N^{th}$ strings into a $(P+1)^{th}$ one of the string groups when said each of the first to $N^{th}$ strings is not smaller in lexicographical order than a $P^{th}$ one of the splitter strings; and
assign said each of the first to $N^{th}$ strings into a $j^{th}$ one of the string groups when said each of the first to $N^{th}$ strings is not smaller in lexicographical order than a $(j-1)^{th}$ one of the splitter strings and is smaller in lexicographical order than a $j^{th}$ one of the splitter strings, where j=2, 3, . . . , P.

13. The system of claim 12, wherein the assignment for each of the first to $N^{th}$ strings is performed using binary search.

14. The system of claim 8, wherein said FM-index data generation module is coupled to said storage module, and is configured to store the FM-index data in said storage module completely; and
wherein said searching module is coupled to said storage module for reading the FM-index data stored in said storage module.

15. The system of claim 8, wherein the FM-index data structure includes:
the suffix array;
an F table including first to $N^{th}$ F table addresses which respectively correspond to the sorted first to $N^{th}$ suffixes in order and each of which records a first one of the characters of the corresponding one of the sorted first to $N^{th}$ suffixes;
a CNT table including a plurality of CNT-table addresses, each of which corresponds to a respective one of the base-related character types and records information relating to a start address in the F table for the respective one of the base-related character type;
an L table including first to $N^{th}$ L table addresses which respectively correspond to the sorted first to $N^{th}$ suffixes in order and each of which records a last one of the characters of the corresponding one of the sorted first to $N^{th}$ suffixes; and
an OCC table including, for each of the base-related character types, first to $N^{th}$ OCC-table addresses that respectively correspond to the first to $N^{th}$ L-table addresses in order; and, for each of the base-related character types, each of the first to $N^{th}$ OCC-table addresses records a number of occurrences of the base-related character type accumulated from the first L table address to one of the first to $N^{th}$ L-table addresses that corresponds to the OCC-table address;
wherein said FM-index data generation module is coupled to said storage module, and is configured to store in said storage module a part the FM-index data which includes the CNT module, the L table, a part of the suffix array and a part of the OCC table; and
wherein said searching module is coupled to said storage module for reading the part of the FM-index data stored in said storage module, and is configured to re-construct the FM-index data using an FM-index data reconstruction algorithm.

16. The system of claim 15, wherein said FM-index data generation module is configured to down-sample the suffix array by retaining the first SA address from every T1 number of the first to $N^{th}$ SA addresses to obtain the part of the suffix array, and to down-sample the OCC table by retaining, for each of the base-related character types, the first OCC-table address from every T2 number of the first to $N^{th}$ OCC-table addresses to obtain the part of the OCC table; and
wherein the FM-index data is re-constructed according to:

$$OCC[n_{occ}, s] = OCC_D\left[\left\lfloor \frac{n_{occ}}{T2}, s \right\rfloor\right] + L\left[\left(\left\lfloor \frac{n_{occ}}{T2} \right\rfloor + 1, n_{occ}\right), s\right]; \text{ and}$$

$$SA[n_{SA}] = SA_D[CNT[L[n_{SA}]] + OCC[n_{SA}, L[n_{SA}]]] + 1,$$

where $n_{occ}$ represents an arbitrary one of the first to $N^{th}$ OCC-table addresses; s represents an arbitrary one of the base-related characters; OCC[.] represents a result of indexing operation on the OCC table; $OCC_D$ [.] represents a result of indexing operation on the part of the OCC table; L[.] represents a result of indexing operation on the L table; $n_{SA}$ represents an arbitrary one of the first to $N^{th}$ SA addresses; SA[.] represents a result of indexing operation on the suffix array; $SA_D$ [.] represents a result of indexing operation on the part of the suffix array; and CNT[.] represents a result of indexing operation on the CNT table.

17. The system of claim 8, wherein the target string is represented by characters of $S_1$ to $S_M$ that are arranged in the given order, where $1 \leq M \leq N$;
  wherein the FM-index data includes:
    the suffix array;
    an F table including first to $N^{th}$ F table addresses which respectively correspond to the sorted first to $N^{th}$ suffixes in order and each of which records a first one of the characters of the corresponding one of the sorted first to $N^{th}$ suffixes;
    a CNT table including a plurality of CNT-table addresses, each of which corresponds to a respective one of the base-related character types and records information relating to a start address in the F table for the respective one of the base-related character type;
    an L table including first to $N^{th}$ L table addresses which respectively correspond to the sorted first to $N^{th}$ suffixes in order and each of which records a last one of the characters of the corresponding one of the sorted first to $N^{th}$ suffixes; and
    an OCC table including, for each of the base-related character types, first to $N^{th}$ N number OCC-table addresses that respectively correspond to the first to $N^{th}$ L-table addresses in order; and, for each of the base-related character types, each of the first to $N^{th}$ OCC-table addresses records a number of occurrences of the base-related character type accumulated from the first L table address to one of the first to $N^{th}$ L-table addresses that corresponds to the OCC-table address;
  wherein said searching module is configured to perform the DNA sequence alignment according to:

$S[i]=S_{(M-i)+1}$, where $i=1,2,\ldots,M$;

$\mathrm{index}_{min}[i]=CNT[S[i]]+OCC[\mathrm{index}_{min}[i-1]-1,S[i]]+1$; and $\mathrm{index}_{max}[i]=CNT[S[i]]+OCC[\mathrm{index}_{max}[i-1],S[i]]$ where S[i] represents one of the characters of the target string to be searched for in an $i^{th}$ iterative searching operation; $\mathrm{index}_{min}[i]$ represents a lower limit for the first to $N^{th}$ SA addresses obtained by the $i^{th}$ iterative searching operation; $\mathrm{index}_{max}[i]$ represents an upper limit for the first to $N^{th}$ SA addresses obtained by the $i^{th}$ iterative searching operation; CNT[.] represents a result of indexing operation on the CNT table; OCC[.] represents a result of indexing operation on the OCC table; $\mathrm{index}_{min}[0]$ is defined as zero; $\mathrm{index}_{max}[0]$ is defined as $N-1$; and $OCC[-1,S[1]]$ is defined as zero; and
  wherein said searching module is configured to, after the $i^{th}$ iterative searching operation:
    perform, when i is not greater than M, an $(i+1)^{th}$ iterative searching operation upon determining that $\mathrm{index}_{min}[i] \leq \mathrm{index}_{max}[i]$;
    output the first alignment result upon determining that $\mathrm{index}_{min}[i] > \mathrm{index}_{max}[i]$;
    output the second alignment result upon determining that $\mathrm{index}_{min}[M] = \mathrm{index}_{max}[M]$, wherein the at least one target index includes one and only one target index which is one of the first to $N^{th}$ location indices that corresponds to either $\mathrm{index}_{min}[M]$ or $\mathrm{index}_{max}[M]$ for the suffix array; and
    output the second alignment result upon determining that $\mathrm{index}_{min}[M] < \mathrm{index}_{max}[M]$, wherein the at least one target index includes a plurality of the target indices each of which is one of the first to $N^{th}$ location indices that corresponds to a respective one of the first to $N^{th}$ SA addresses which is not smaller than $\mathrm{index}_{min}[M]$ and which is not greater than $\mathrm{index}_{max}[M]$.

18. The system of claim 7, wherein said string sorting module includes C number of sorting elements connected in a cascade manner, each of said sorting elements includes:
  a buffer having an input terminal, a control terminal and an output terminal, and configured to temporarily maintain a current data;
  a comparator having a first input terminal disposed to receive to-be-sorted data, a second input terminal coupled to said output terminal of said buffer of said sorting element, and an output terminal coupled to said control terminal of said buffer of said sorting element; and
  a 2-to-1 multiplexer having a first input terminal coupled to said first input terminal of said comparator of said sorting element, a second input terminal coupled to said output terminal of said buffer of an immediate previous one of said sorting elements, a control terminal coupled to said output terminal of said comparator of the immediate previous one of said sorting elements, and an output terminal coupled to said input terminal of said buffer of said sorting element;
  wherein, for each of said sorting elements, said comparator is configured to output, upon determining that the to-be-sorted data is greater in lexicographic order than the current data at said output terminal of said buffer, an enable signal to said control terminal of said buffer of said sorting element and said control terminal of said 2-to-1 multiplexer of an immediate next one of said sorting elements through said output terminal thereof, such that:
    said 2-to-1 multiplexer of the immediate next one of said sorting elements outputs the current data received from said buffer of said sorting element in response to the enable signal; and
    said buffer of said sorting element outputs, at said output terminal thereof in response to the enable signal, data received from said 2-to-1 multiplexer of said sorting element through said input terminal thereof;
  wherein, for each of said sorting elements, said comparator is configured to output, upon determining that the to-be-sorted data is smaller in lexicographic order than the current data at said output terminal of said buffer, a disable signal to said control terminal of said buffer and said control terminal of said 2-to-1 multiplexer of the immediate next one of said sorting elements through said output terminal thereof, such that:
    said 2-to-1 multiplexer of the immediate next one of said sorting elements outputs the to-be-sorted data in response to the disable signal; and
    said buffer of said sorting element maintains the current data in response to the disable signal; and
  wherein said string sorting module is configured to receive the first to $N^{th}$ strings one by one from said string generation module to serve as the to-be-sorted data.

19. The system of claim 18, wherein said string sorting module further includes an A-to-1 multiplexer that has A number of input terminals, a control terminal disposed to receive a control signal relating to a total number of the to-be-sorted data, and an output terminal, wherein an $m^{th}$ one of said input terminals of said A-to-1 multiplexer is coupled to said output terminal of said buffer of an $(m \times B)^{th}$ one of said sorting elements, where $m=1, 2, \ldots, A$; and wherein said A-to-1 multiplexer is configured to, in response to the control signal:

establish electrical connection between a first one of said input terminals thereof and said output terminal thereof when $D \leq B$, where D represents the total number of the to-be-sorted data;

establish electrical connection between an $(n+1)^{th}$ one of said input terminals thereof and said output terminal thereof when $n \times B < D \leq (n+1) \times B$, where $n = 1, 2, \ldots, A-1$; and establish electrical connection between an $A^{th}$ one of said input terminals thereof and said output terminal thereof when $C < D < 2C$.

20. The system of claim 19, wherein, when $C < D < 2C$, said string sorting module performs sorting again on (D−C) ones of the to-be-sorted data which are first outputted thereby after completion of the sorting of all of the D number of to-be-sorted data.

\* \* \* \* \*